United States Patent
Viirre

[19]

[11] Patent Number: 6,003,991
[45] Date of Patent: Dec. 21, 1999

[54] EYE EXAMINATION APPARATUS AND METHOD FOR REMOTE EXAMINATION OF A PATIENT BY A HEALTH PROFESSIONAL

[75] Inventor: Eric Viirre, Seattle, Wash.

[73] Assignee: Erik Scott Viirre, San Diego, Calif.

[21] Appl. No.: 08/799,859

[22] Filed: Feb. 13, 1997

Related U.S. Application Data

[60] Provisional application No. 60/011,939, Feb. 17, 1996.

[51] Int. Cl.⁶ ........................................................ A61B 3/10
[52] U.S. Cl. ............................ 351/206; 351/205; 351/246
[58] Field of Search ...................................... 351/246, 205, 351/210, 209, 211, 221, 200; 364/516.444, 571.414

[56] References Cited

U.S. PATENT DOCUMENTS 5,583,795  12/1996  Smyth ................................ 364/516.444

*Primary Examiner*—Hung Xuan Dang
*Attorney, Agent, or Firm*—Sheridan Ross P.C.

[57] ABSTRACT

A stereo HMD with an in-dwelling video camera at a patient site, and a stereo camera at a doctor's site are provided for performing examinations of a patient's eyes over a video link. The patient wears the stereo HMD with cameras. Over the video link, images of the patient's eyes are sent to the doctor. The doctor is positioned in front of a stereo camera and an image of the doctor is sent back to the patient for display on the HMD. The doctor can view the external eye structures and can direct the patient to look in various directions. The doctor may move an object in the direction desired. The doctor views the response on a monitor. The doctor may control light to each eye of the patient by covering the appropriate lens of the stereo camera. By alternately covering left and right cameras, the "swinging flashlight" test can be done. Slit light sources built into the HMD are provided to illuminate the front portions of the eyeball, i.e., the anterior chamber, for examination.

19 Claims, 5 Drawing Sheets

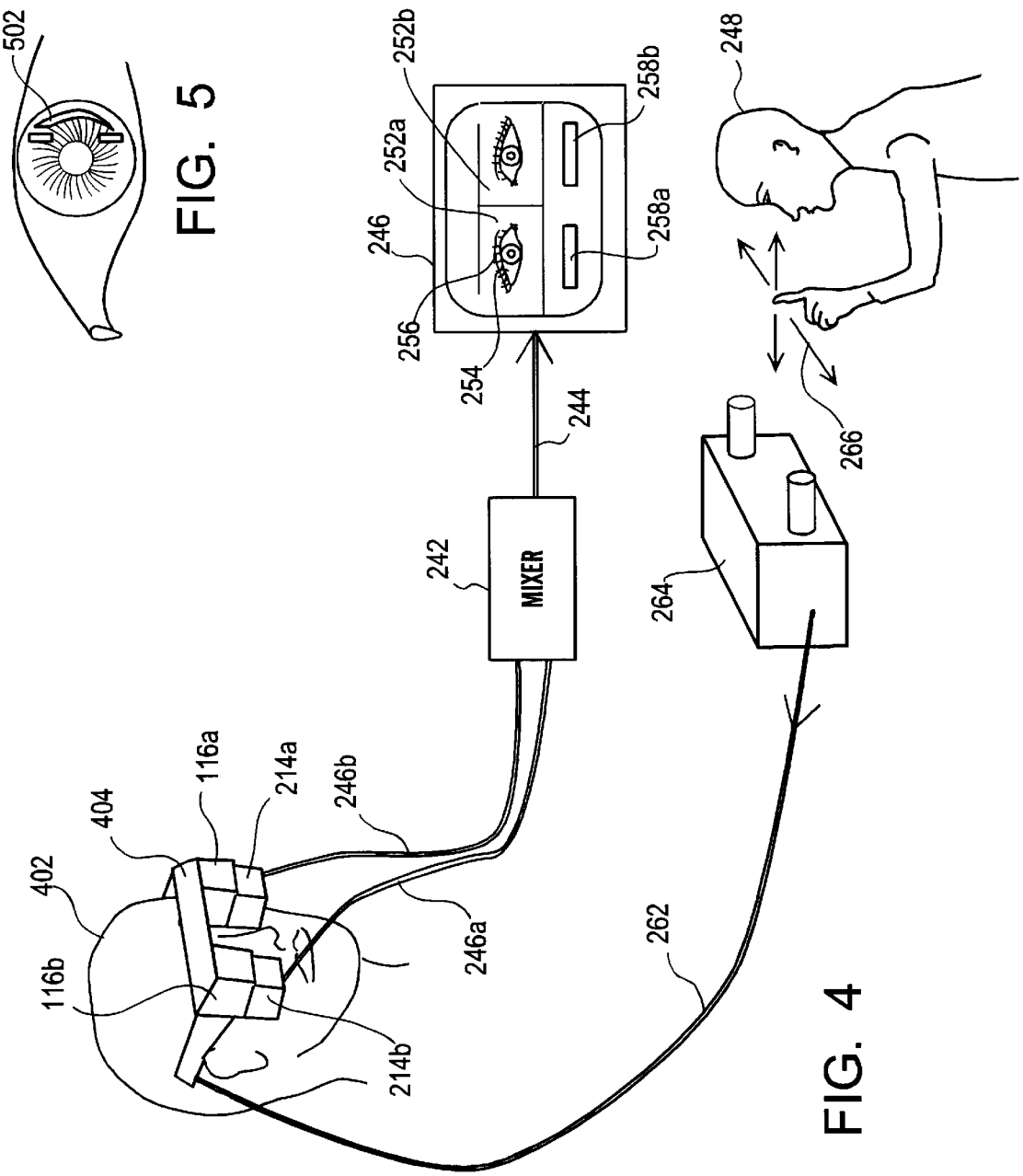

METHOD ONE.

METHOD TWO.

METHOD THREE.

IMAGE-SOURCE-DETECTOR OVERLAY

EYE EXAMINATION APPARATUS AND METHOD FOR REMOTE EXAMINATION OF A PATIENT BY A HEALTH PROFESSIONAL

The present application claims priority in U.S. provisional application Ser. No. 60/011,939, filed Feb. 17, 1996 for VIDEO EYE EXAMINATION APPARATUS AND METHOD, commonly assigned herewith and incorporated herein by reference.

The present invention relates to an apparatus and method for performing ophthalmic or other eye examination for medical or veterinary diagnosis, treatment or research, and in particular to a head-mounted display with sensors coupled thereto and method for use.

BACKGROUND INFORMATION

A number of devices have been developed for use in medical or veterinary examinations, some of which can be applied in a telemedicine context, i.e., in which data or results from the examination are transmitted over an electronic or other communication link (e.g., via telephone line, radio communication, etc.) so that the physician or other medical worker need not be in the same location as the patient. For example, the video otoscope may be used to examine the external ear canal and eardrum of a patient in a remote location.

Because of present concerns for the cost of medical care, it would be preferable to provide devices for telemedicine which help contain the costs for such procedures. Because it is anticipated that some telemedicine may be practiced relative to patients who cannot readily move to central medical facilities (e.g., patients who are in extremely remote areas, inaccessible locations such as aircraft or spacecraft, "third world" regions where medical facilities are sparse, or who are in combat or other dangerous situations) such telemedicine devices preferably are sufficiently rugged, light-weight and reliable that they can be easily sent to such remote and/or dangerous locations with little need for maintenance or repair.

Numerous medically valuable examinations involve examination of the external eye, often including examination of the lids and lashes as well as the physical structures of the eyeball (globe). For examination of the pupilliary response, a light is shown in each eye alternately. Each pupil should constrict when light is on and dilate when light goes off. The pupil responses should be the same in each eye. To study the movements of the eyes, the subject follows a moving target (often the examiner's finger) and holds the direction of gaze in various positions: center, up, down, left, right, approaching the eye and away from the eye. The eye is examined for abnormal movements called nystagnus or other abnormalities. The character of any nystagnus indicates possible disease in the brain or the brain's movement sensors.

Accordingly, it would be useful to provide an apparatus and method for examination of a patient's eyes, permitting, where desired, remote examination, preferably using a reliable, rugged, low-maintenance, and relatively low-cost apparatus.

SUMMARY OF THE INVENTION

According to the present invention, a head-mounted device is provided which includes one or more displays and/or light sources for providing visual stimulation and/or illuminating either or both of the patient's eyes and includes one or more cameras or other sensors for sensing and/or recording data. The sensed data may be transmitted to a remote location, e.g., for viewing by a physician. In one embodiment, a camera, preferably a stereo camera, images the physician (or otherwise can be used to provide visual stimuli) and this image is transmitted over a telecommunications link to the patient for display on the display device of the head-mounted unit.

In one embodiment, a stereo HMD with an in-dwelling video camera at a patient site, and a stereo camera at a doctor's site are provided for performing examinations of a patient's eyes over a video link. The patient wears the stereo HMD with cameras. Over the video link, images of the patient's eyes are sent to the doctor. The doctor is positioned in front of a stereo camera and an image of the doctor is sent back to the patient for display on the HMD. The doctor can view the external eye structures and can direct the patient to look in various directions. The doctor may move an object in the direction desired. The doctor views the response on a monitor. The doctor may control light to each eye of the patient by covering the appropriate lens of the stereo camera. By alternately covering left and right cameras, the "swinging flashlight" test can be done. Slit light sources built into the HMD are provided to illuminate the front portions of the eyeball, i.e., the anterior chamber, for examination.

BRIEF DESCRIPTION OF THE DRAWINGS

FIG. 4 is a perspective conceptual view of a remote eye examination apparatus according to an embodiment of the present invention;

FIG. 5 is a front plan view of the patient's eye with light sources according to an embodiment of the present invention;

DETAILED DESCRIPTION OF THE PREFERRED EMBODIMENTS

In the embodiment in FIG. 4, a head-mounted display (HMD) 102 is coupled to left and right cameras 104 for, respectively, imaging the left and right eyes of the user of the head-mounted display 102. A number of head-mounted displays can be used including those described in PCT/US94/09819 filed Aug. 31, 1994 for Personal Visual Display System (corresponding to U.S. Ser. No. 08/416,919), PCT/US95/11344 filed Aug. 31, 1995 for Personal Display System (corresponding to U.S. Ser. No. 08/484,857 is the U.S. national phase) and U.S. patent application Ser. No. 60/002,013 "Head-Mounted Display With Eye Tracking" filed Aug. 8, 1995, all of which are commonly assigned herewith and incorporated herein by reference. As depicted in FIG. 4, a user 402 has mounted on his or her head an HMD 404. In one embodiment the HMD provides left and right displays with associated optics for conveying left and right images to the user's left and right eyes. In one embodiment, the HMD 404 contains two separate image generators such as two separate LCD devices so that binocular or, preferably, stereoscopic displays can be provided to the user 402.

Figure 6A:
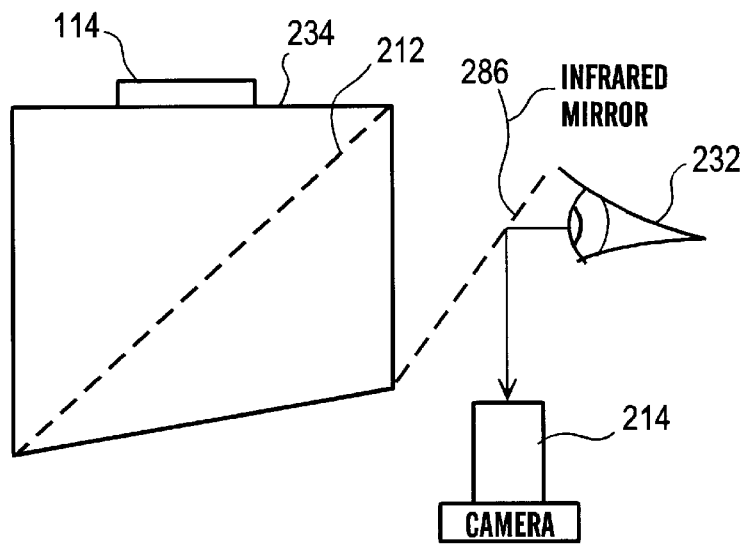
FIGS. 6A through 6C are schematic side cross-sections showing camera placement according to embodiments of the present invention.

In the embodiment depicted in FIG. 6C, an LCD image generator 114 outputs an image, e.g., one-half of a stereo image generated as described below, downwards towards a fold mirror 212. The fold mirror 212, in one embodiment, reflects the image from image generator 114 to a reflective front surface 116 which may, if desired, be a concave reflector to provide for image enlargement. The image reflected from reflector 116 is then transmitted through fold mirror 212, which may be a half-silvered mirror, to the user's eye 232. In the embodiment of FIG. 6C a camera 214 is mounted below the fold mirror 212 and receives an image of the user's eye 232 reflected off the bottom surface of the fold mirror 212.

Because, in this embodiment, there is no need for positioning apparatus between the HMD "shroud" 234 and the user's eye 232, there is a certain amount of space or "eye relief" 236 preferably sufficient to accommodate eyeglasses so that the physician may, if desired, perform tests on the patient while the patient is wearing eyeglasses or may request that the patient remove eyeglasses.

If desired, the eye may be imaged by the camera 214 at a wavelength different from the wavelength of light transmitted to the eye from the image source 114. For example, the camera 214 may be an infrared camera. In this case, it may be preferred to interpose an infrared filter 218 below the image source 114 and/or to interpose a visible light filter 222 in the optical path prior to the camera 214 in order to avoid transmitting, to the camera 214, infrared light which originated in the image source 114 or visible light, from any source.

The fold mirror 212 may be visible-reflective on the upper surface and infrared-reflective on the bottom surface. It is also possible to use a mirror 112 which reflects both visible and infrared light. A phase-shift mirror is available from Melles Girot as Product 12PSM003. As an infrared filter 218, Model RG830 available from Melles Girot Company can be used. As a visible filter 222, a filter that removes light below 840 NM in wave length, e.g., Model BG38, available from Melles Girot Company can be used.

In one embodiment reflector 116 is at least partially transmissive to provide the patient with a view of the world through the reflector 116. In another embodiment, the user is prevented from seeing any view of the world through reflector 116.

Preferably, left and right cameras 214a, b are provided to separately image the left eye and right eye. In the embodiment of FIG. 4, the signals are transmitted from the cameras 214a, 214b to a mixer 242 so the signals from the left and right cameras can be transmitted over a single communication link 244, e.g., via multiplexing. The lines 246a, b may emerge directly from the camera locations 214a, 214b or may be routed, via a harness, etc., to emerge from another location on the HMD 404. The lines 246a, 246b may be cables, optical fibers, and the like. Signals from the cameras may also be transmitted via infrared, radio or other wireless links. Similarly, communication channel 244 may be a cable, an optical fiber, a telephone link, local area network link, wide area network link, cellular telephone link, infrared, radio, or other wireless link.

The images of the patient's left and right eyes are preferably displayed on a monitor 246 for viewing by the physician 248. In the depicted embodiment, the left and right eyes images are displayed in left and right central portions 252a, 252b of the monitor 246. In the depicted embodiment, the images include substantially the entire eye of the patient include eyelid 254, and lashes 256. In one embodiment, cameras 214a, 214b can be configured to provide 2 or more different magnifications (or to provide for a "zoom" facility) so that the physician may see one or both of the user's eyes in a more magnified view. Magnified or zoomed images may also be provided by electronic or software associated with the monitor 246 or cameras 214a, 214b. For large "zoom" sizes, it may be preferable to image only a single eye of the pupil on the monitor 246. Preferably, regions 258a, 258b are provided on the monitor 246 for supplying additional data to the physician, as described below.

In order to allow the physician to perform certain types of tests, a second communication link 262 is provided for transmitting an image from a camera, preferably a stereo television camera 264 over the communication link 262 to the head-mounted display 102 for generating the images for viewing by the patient's left and right eyes. Thus, in the embodiment of FIG. 4, the physician 248 may move a finger or other object to be visually tracked by the patient 402 while the physician 248 views the monitor 246 to watch the movement of the patient's eyes.

Figure 1:
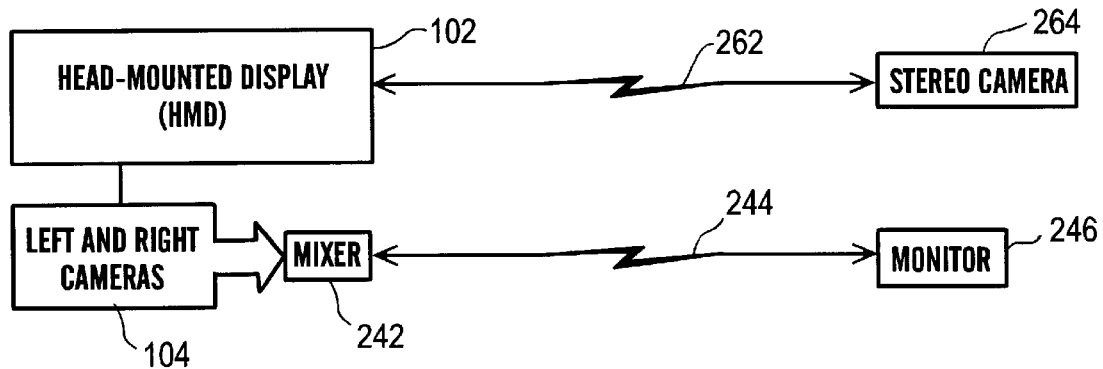
FIG. 1 is a block diagram depicting an eye examination apparatus according to an embodiment of the present invention.
Figure 2:
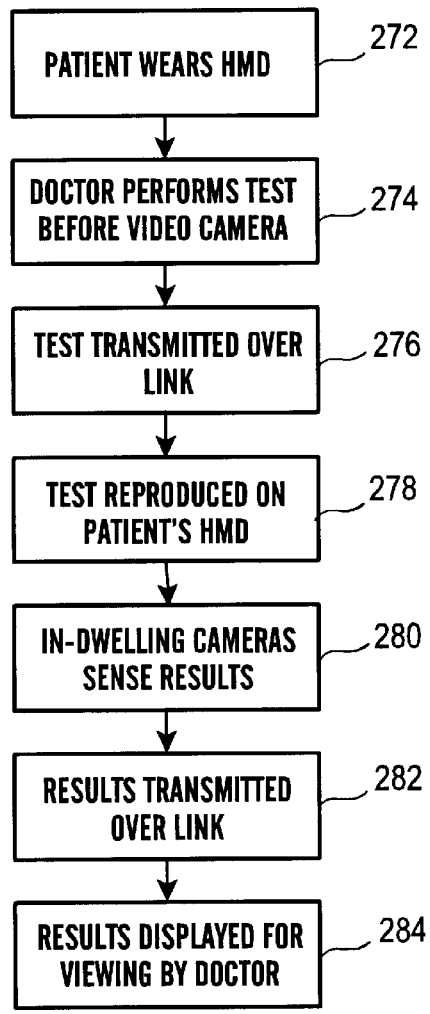
FIG. 2 is a flow chart showing an eye examination method according to an embodiment of the present invention.
Figure 3:
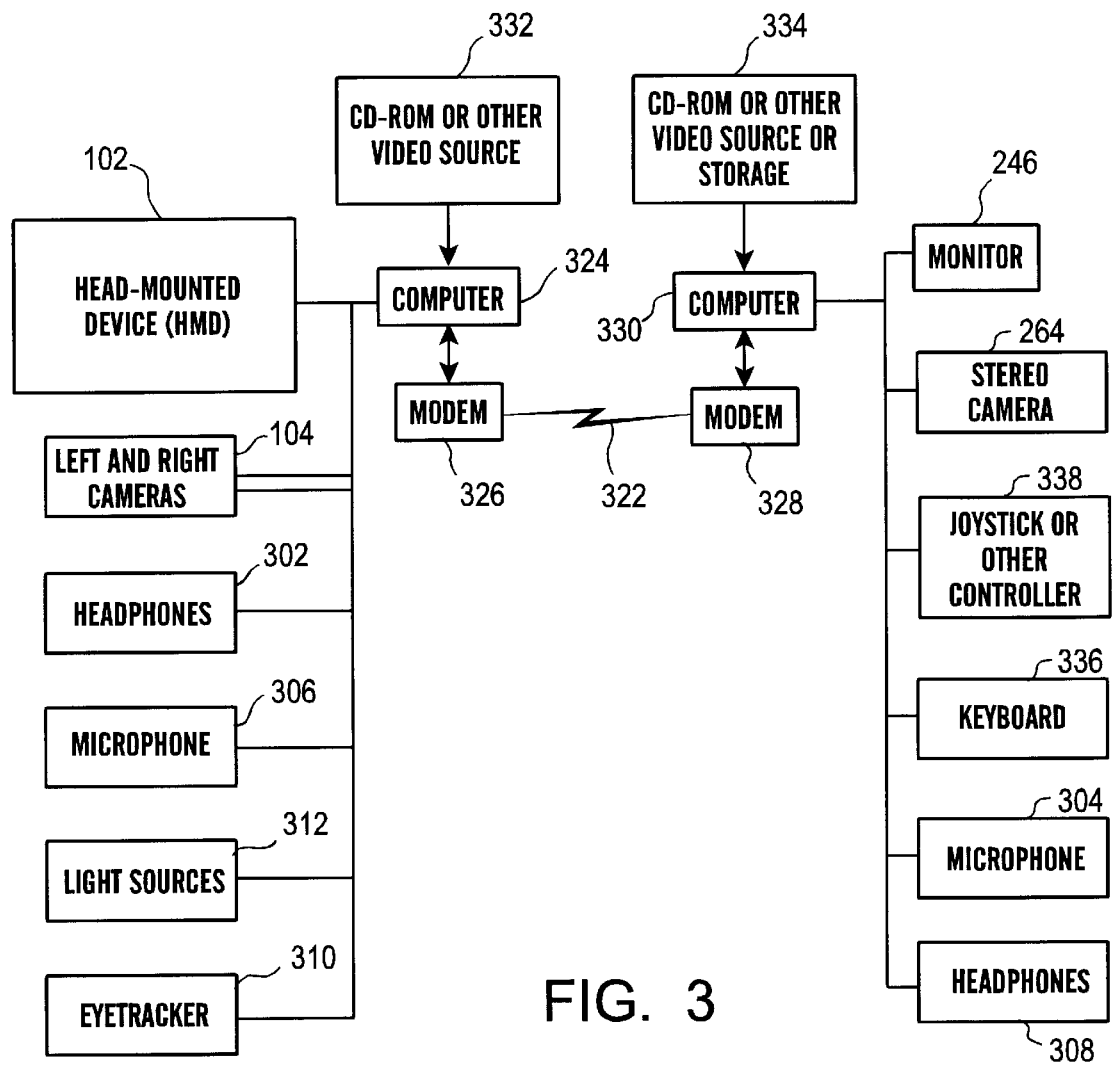
FIG. 3 is a block diagram showing an eye examination apparatus and system according to an embodiment of the present invention.

In operation, as shown in FIG. 2, the patient 402 first puts on the HMD 272. The doctor 248 performs a test such as moving a finger 266 before the video camera 274. This vision test is captured by the camera 264 and transmitted over the telecommunications link 276. This test is reproduced on the patient's HMD by displaying the moving stereoscopic image using the left and right image generators 114 of the HMD 278. The in-dwelling cameras 214a, 214b image or otherwise sense the results of the test 280. These results are transmitted over a communication link 244 to permit results to be viewed by the physician 282. The results are then displayed on the monitor 246 so that the physician 248 may perceive how the patient 402 responds to the test 284.

A number of other embodiments of the present invention can also be used. For example, there are numerous other ways in which eye movement or characteristics may be imaged or sensed. In the embodiment of FIG. 6A, an infrared mirror 286 is positioned between the shroud 234 and the eye of the patient 232 so that an infrared image is transmitted downward toward camera 214. Use of an infrared image of the eye is useful in accommodating variations in visible light and also allows measurement in the dark. A number of types of infrared cameras or detectors can be used including a charge couple device (CCD) camera such as that available from Marshall Electronics as Model 1204. If desired, a visible light camera 214 can also be used.

Figure 6B:
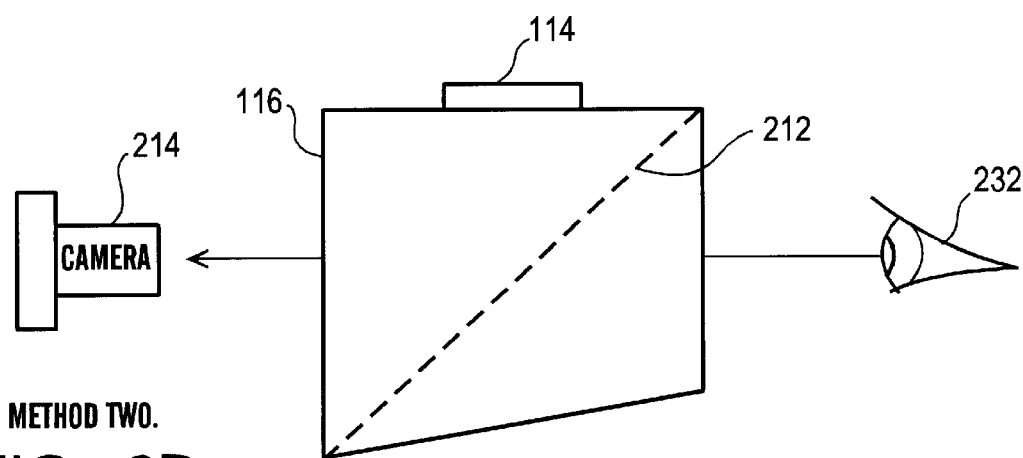
Figure 6C:
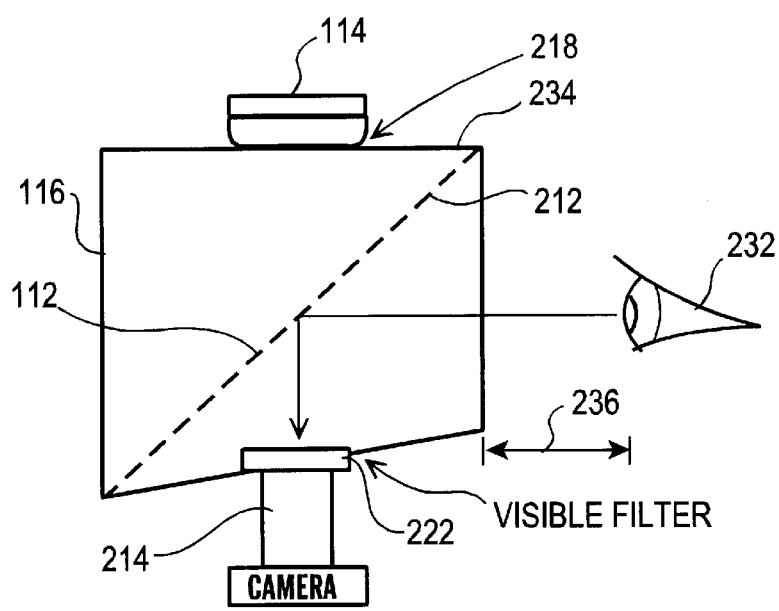

In the configuration of FIG. 6B, the image of the user's eye is captured directly through the fold-mirror 212 by placing the camera 214 in front of the second deflector 116 which is at least partially transmissive. This configuration would normally interfere with direct viewing of the environment by the user. This aspect can be at least partially modified by mounting an infrared mirror in the position depicted in FIG. 6B for the camera 214 to reflect the infrared image to a camera located elsewhere, and in which the infrared mirror is at least partially transmissive to visual light to permit the user the have a view of the environment.

Although in the depicted embodiment the cameras 214 are configured to provide an image which can be displayed on the monitor 246 and viewed by a physician, it is also possible to provide for detectors 214a, 214b which, in place of or in addition to providing a visible image, automatically measure or detect characteristics or parameters of the eye such as the location of the patient's pupil within the field of view. Thus, in one embodiment, it is possible to display data, such as text indicating the X, Y positions of the pupils, e.g., in regions 258a, 258b of the monitor. Such data may also be displayed in place of or superimposed over the images of the eyes 252a, 252b. It may also be useful to superimpose data from, e.g., an eye-tracker on the eye images, e.g., by displaying cross-hairs over the eye image at the pupil's center, fovea, etc. If desired, another image may be positioned adjacent the eye images, e.g., in areas 258a, 258b, e.g., images of normal eye responses provided, e.g., from a CD ROM 334 or other video source. Methods for detecting pupil position are described, e.g., in copending patent application Ser. No. 60/002,013, supra.

Figure 7:
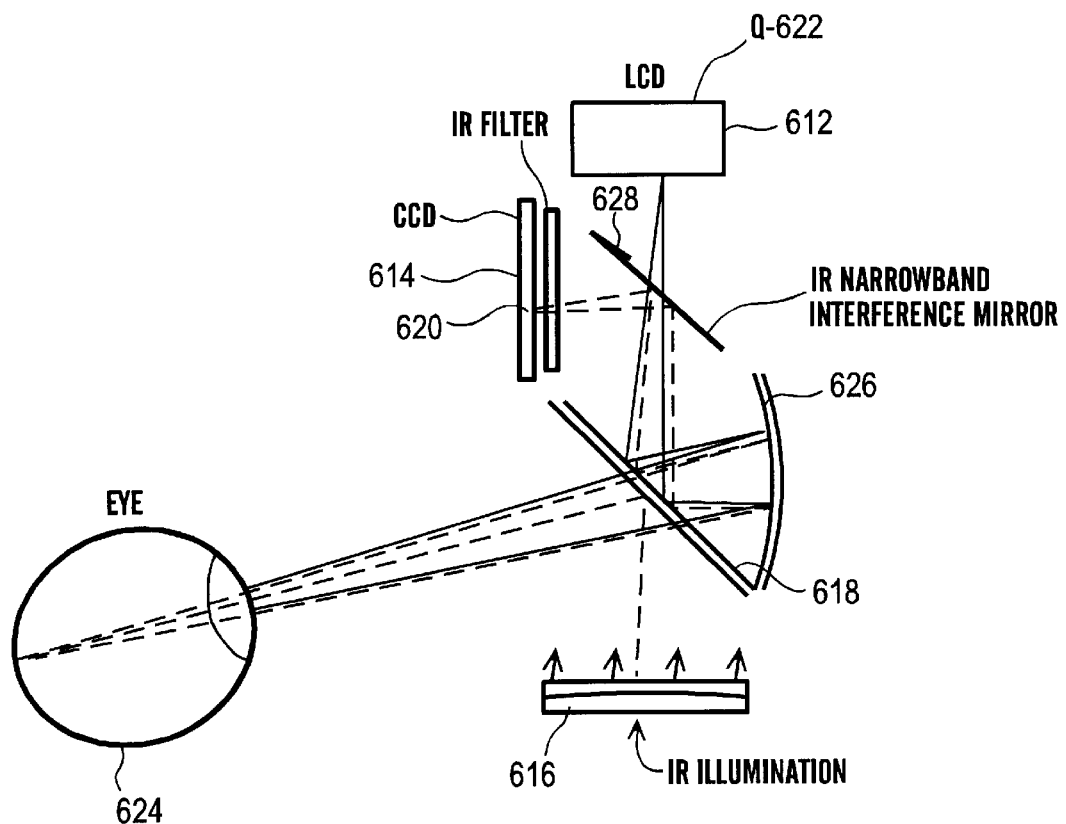
FIG. 7 is a schematic cross-section showing a charge-coupled detector according to an embodiment of the present invention.

In the embodiment of FIG. 7 an IR illumination source 616 is located below the fold mirror 618. IR light from IR sources 616 reflects off the lower surface of the fold mirror 618 (or alternatively, a separate mirror) into the user's eye. The IR light then reflects from the retina, travels along an optic path (described below) and is focused at a point Q 620 of the CCD which corresponds to the point Q 622 of the image plane 612 that is being observed by the eye 624. The optic path of the IR light from the eye in this embodiment is through the fold mirror 618, reflected off the second reflector of 626, reflected upward by the fold mirror 618 towards an IR narrow band interference mirror 628 and then to the CCD 614. Because of the one-to-one correspondence of the CCD to the LCD, the point Q that is being observed by the eye on the LCD has the fovea imaged in IR on a corresponding location in the CCD. Thus, the embodiment of FIG. 7 may be used to track the position of the fovea, rather than the pupil position.

Figure 8:
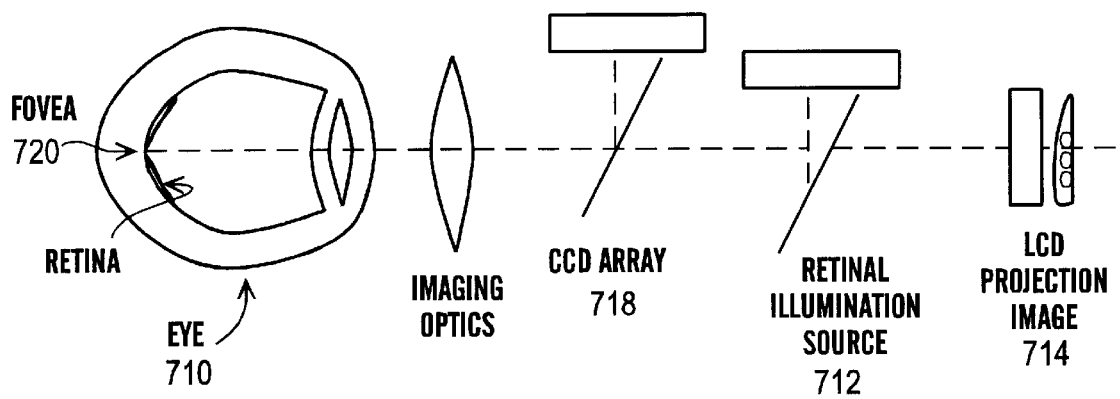
FIG. 8 depicts a fovea detection device according to an embodiment of the present invention.

In the embodiment of FIG. 8, a similar concept is employed, but the embodiment is somewhat different. In FIG. 8, the IR retinal illumination source 712 is positioned between the image source 714 and the CCD array 718.

In addition to the components depicted in FIG. 4, other components may be provided either for use by the patient or for use by the physician. In one embodiment, the user is provided with headphones 302 and the physician with a microphone 304 so that the physician may provide communications to the patient. Similarly, the patient may be provided with a microphone 306 and the doctor with headphone 308 (or speakers, not shown) for receiving spoken information from the patient. Rather than, or in addition to, providing cameras 104, the patient device may provide an automatic eye tracker 310 which provides information about eye movement. The patient device may be provided with various controllable light sources 312, e.g., slit light sources so that the front portion of the eyeball (the "anterior chamber") can be imaged 502 and examined by the physician as depicted, e.g., in FIG. 5.

A number of methods of providing for data communication can be used. Rather than providing 2 separate data links 262, 244, a single duplex link 322 may be provided. For example, the data to and from the head-mounted display 102 may be communicated from and to a computer 324 located at the patient site and having a modem 326 for communication with a modem 328 at the doctor's location. The modem 328 at the doctor's location may communicate with a computer 330 for driving a monitor 246, receiving images from a stereo camera 264, etc. Manners of receiving and transmitting images and other data using computers are well-known in the multi-media computer art.

Although it is contemplated that the present invention is useful for remote or telemedicine, it is also possible for the HMD of the present invention to be used when the patient and the doctor are in the same location, e.g., by the patient wearing the headset while the doctor initiates tests using the stereo camera 264, providing spoken instructions to the patient, and the like.

It is possible to provide images for display to the patient using the HMD which originate from a source other than a camera 264. For example, it may be useful to synthesize or generate images, such as images of a moving light, a "virtual finger", etc. for display on the HMD 102. Such images may be generated by computer 394 or prerecorded and played back from a CD ROM, videotape or other video source 3032 connected to the patient-location computer 324 or a source 334 connected to the physician-location computer 330. For remote or telemedicine purposes, the images to be generated may be controlled by the physician using a keyboard 336, joystick, mouse or other controller 338. For example, rather than moving a finger 266 adjacent to stereo camera 264, the apparatus may be configured such that the physician may move a joystick 338 and the computer 324 will generate an image of a light or other target which moves in response to movement of the joystick. Manners of generating moving images in response to movement of a joystick or other controller are well-known in the art. In situations in which the physician is located at the same place as the patient, the physician may use a keyboard, joystick, etc. coupled to the patient-location computer 324 to generate the desired images.

In order to separately test the patient's eyes, in the embodiment of FIG. 4 the physician may cover one of the lenses of the stereo camera 264 and thus "black out" one eye of the user. Alternatively, the physician may use a keyboard 336, joystick 338, etc. to instruct the computer 324, 330 to control the HMD such that only one image generator 114 is generating an image. Although a stereo camera 2624 is preferred, it is also possible to use a monoscopic camera and provide a single image to both eyes or to synthesize or simulate a 3-dimensional image based on the monoscopic camera data. In addition to or in place of displaying the images of the patient's eyes in real time, the images may be recorded, e.g., on a VCR or other video storage device 234 (or on a device connected to computer 324 or HMD 102) for later playback. This may be useful for performing a test (either generated automatically or performed by or under the direction of a technician) for later review and analysis by a physician. Recorded tests or results can also be used for physician or technician training. Such a recorded image may also be useful for keeping as part of a patient's medical records and/or for later review by a specialist or other consulting physician.

The image which the patient perceives may be an image which is generated or recorded so as to provide for one or more standardized tests. By providing standardized tests, it can be known that substantially identical tests are shown to two or more patients. Standardizing certain tests may permit these tests to be performed by technicians rather than physicians. An HMD may be provided with an in-dwelling video source and/or an in-dwelling video recorder so that, for example, the device may be used to test each student in a grade school classroom and record that student's responses (along with the student identification) and the recorded data may be later efficiently and rapidly reviewed by a physician (or screened by a technician).

Although a monitor 246 is depicted for displaying the eye images or other data to the physician, it may be desirable for the physician 248 to view the images through a head-mounted display. By providing for head-mounted display viewing, it is possible to simultaneously display substantially the same image on numerous head-mounted displays so that several physicians may simultaneously view the same test results from the same perspective.

In light of the above description, a number of advantages to the present invention can be seen. The present invention permits a physician or other health professional to perform certain eye examinations on a patient who may be remotely located. The present invention provides the potential for augmenting visual examinations of the patient's eyes with certain objective measurements such as a pupil position, fovea position, etc. The present invention permits eye examination data to be recorded for later playback or to be made part of the patient's records. The present invention makes possible the creation of standardized eye tests and/or tests which may be performed by non-physicians for later review by health professionals.

Although the invention has been described by way of a preferred embodiment and certain variations and modifications, other variations and modifications can also be used, the invention being defined by the following claims.

What is claimed is:

1. Apparatus usable for eye examination of a patient comprising:
    head-mounted means having at least a first image generator for providing an image to at least a first eye of said patient;
    an image source for providing an image to be generated by said image generator;
    camera means for obtaining a first video image of at least said first eye of said patient, and for obtaining a second video image of a second eye of said patient, said camera means being coupled to said head-mounted means; and
    wherein said patient is remotely located from a physician and further comprising means for transmitting both said first video image and said second video image over a communication link to a location where both said video image of said first eye of said patient and said video image of said second eye of said patient are displayed for viewing by said physician.

2. Apparatus as claimed in claim 1 wherein said image generator comprises first and second liquid crystal displays.

3. Apparatus as claimed in claim 1 wherein said image source comprises a stereo camera.

4. Apparatus as claimed in claim 1 wherein said camera means is an infrared camera.

5. Apparatus as claimed in claim 1 further comprising means for recording at least one of said first and second video images of said patient's eyes transmitted over said communication link.

6. Apparatus as claimed in claim 1 further comprising an eye tracker.

7. Apparatus as claimed in claim 1 further comprising means for transmitting sound signals over said communication link and headphone means, coupled to said head-mounted display for providing sound based on said sound signals, to the ears of said patient.

8. Apparatus as claimed in claim 1 further comprising at least a first light source mounted in said lead-mounted display for illuminating a first portion of at least said first eye of said patient.

9. Apparatus as claimed in claim 1 wherein said camera means is a visible light camera.

10. Apparatus as claimed in claim 1 wherein said image source comprises a camera positioned to obtain an image of said physician and wherein said communication link provides said image of said physician to said image generator for display to said patient.

11. Apparatus as claimed in claim 1 wherein said patient is substantially prevented from seeing a view of the world.

12. Apparatus as claimed in claim 1 further comprising a multiplexer for multiplexing said first video image and said second video image.

13. Apparatus as claimed in claim 1 further comprising means for magnifying at least one of said first and second video images for viewing by said physician.

14. Apparatus as claimed in claim 1 wherein each of said first and second video images includes an image of the patients eyelids and eye lashes.

15. Apparatus, as claimed in claim 1, further comprising a microphone adjacent said patient, and wherein spoken information from said patient is provided to said location of said physician.

16. A method for remote eye examination of a patient by a health professional, said patient being remotely located from said health professional, comprising:
    providing a head-mounted display for wearing by said patient, said head-mounted display configured to receive image data and provide said image data to at least a first eye of said patient, and having first and second cameras for obtaining, respectively, a first video image of at least said first eye of said patient and a second video image of a second eye of said patient;
    generating image data for displaying to at least said first eye of said patient using said head-mounted display;
    transmitting both of said first and second video images over a communication link; and
    displaying said first and second video images received over said communication link at a location where said first video image of said first eye of said patient and said second video image of said second eye of said patient are displayed for viewing by said health professional.

17. A method, as claimed in claim 16 further comprising superimposing data over at least one of said first and second video images.

18. Apparatus usable for eye examination of a patient comprising:
    a head-mounted display having at least a first image generator which provides an image to at least a first eye of said patient;
    an image source which provides an image to be generated by said image generator;
    first and second video cameras positioned to provide, respectively, a first video image of at least said first eye of said patient and a second video image of a second eye of said patient, said cameras being coupled to said head-mounted display; and
    wherein said patient is remotely located from a physician and further comprising a transmitter transmitting both said first video image and said second video image over a communication link to a location where both said video image of said first eye of said patient and said video image of said second eye of said patient are displayed for viewing by said physician.

19. Apparatus as claimed in claim 18 further comprising means for generating an image to be displayed by said head-mounted display for viewing by said patient.

* * * * *